US 6,596,307 B1

(12) United States Patent
Brown, Jr. et al.

(10) Patent No.: US 6,596,307 B1
(45) Date of Patent: Jul. 22, 2003

(54) PROCESS FOR PREPARING PHARMACEUTICAL BULK MATERIAL HAVING UNIFORM DISSOLUTION

(75) Inventors: Frank Brown, Jr., West Lafayette, IN (US); Robert Alan Forbes, Clinton, IN (US); Arlette Faye Kreager, Avon, IN (US); Michael Vincent Mullen, Fishers, IN (US); Gregory Alan Stephenson, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/049,540

(22) PCT Filed: Jun. 15, 1999

(86) PCT No.: PCT/US99/13481

§ 371 (c)(1),
(2), (4) Date: Oct. 26, 2001

(87) PCT Pub. No.: WO00/69417

PCT Pub. Date: Nov. 23, 2000

(51) Int. Cl.$^7$ .............................. A61K 9/14; A61K 9/48
(52) U.S. Cl. ....................................... 424/451; 424/489

(58) Field of Search ................................. 424/451, 452, 424/453, 489, 464, 465, 454, 455, 456

(56) References Cited

U.S. PATENT DOCUMENTS

| 4,609,542 A | * | 9/1986 | Panoz et al. .................. 424/19 |
| 4,713,247 A | | 12/1987 | Sakamoto et al. .......... 424/461 |
| 5,693,790 A | | 12/1997 | Da Col et al. ............... 540/220 |

* cited by examiner

Primary Examiner—James M. Spear
(74) Attorney, Agent, or Firm—Tina M. Tucker

(57) ABSTRACT

The present invention provides a process for producing cefaclor crystalline bulk material having a dissolution rate in a capsule of ≧80% in water in 30 minutes. One process route includes reducing the water content of cefaclor dihydrates or bulk material containing cefaclor dihydrate to produce a cefaclor form having a water content ≦2%. The cefaclor having the lower water content can then be rehydrated to a water content from 3.0 to 6.5% without adversely affecting the dissolution rate. An alternative process includes the addition of at least 0.05% of cefaclor related substances to inhibit conversion of the monohydate to the dihydate form.

17 Claims, 2 Drawing Sheets

US 6,596,307 B1

PROCESS FOR PREPARING PHARMACEUTICAL BULK MATERIAL HAVING UNIFORM DISSOLUTION

This application is a 371 of PCT/US99/13481 filed Jun. 15, 1999.

The present invention relates to a process for preparing a pharmaceutical bulk material having more uniform dissolution in water, in particular, uniform dissolution of cefaclor bulk material.

Cefaclor (3-chloro-7-D-(phenylglycinamido)-3-cephem-4-carboxylic acid) is a semi-synthetic, second-generation, cephalosporin antibiotic. Cephalosporins exert their antibacterial activity by reacting with and thereby inactivating one or more of the penicillin-binding proteins located in the bacterial cell wall. Cefaclor is active against a wide range of commonly found pathogens, including S. aureus, β-haemolytic streptococci pneumonococci, Haemophilus influenzae, E. coli, Klebsiella pneumoniae and Proteus mirabilis. The preparation of cefaclor is described in German Patent No. 2,408,698; U.S. Pat. No. 3,925,372; and Chauvette, R. R. and P. A. Pennington, J. Med. Chem, 18, 403 (1975).

Pharmaceutical forms currently available for oral administration of cefaclor include capsules, retard tablets and suspension (both in vial and sachet form). To be useful as a capsule, the USP standard for cefaclor capsules requires at least 80% (Q) of the capsule to dissolve in water in 30 minutes. The dissolution rate is dependent upon the solubility of the active ingredient(s) as well as the excipients used in the formulation and ingredients used in the formation of the capsule. Applicants have observed that capsules prepared from freshly prepared cefaclor monohydrate bulk materials do not consistently meet the USP standard; however, capsules prepared from aged cefaclor monohydrate bulk materials more consistently meet the USP standards. Although acceptable product can be produced from aged materials, the aging process causes several disadvantages. For example, the material is not available for use over an extended period of time, storage costs, and lot to lot variability over time. Therefore, there is a need to provide a process that produces capsules having more uniform and consistent dissolution rates without having to age the bulk active material.

The present invention provides a process for producing cefaclor crystalline bulk form having a dissolution rate in a capsule of ≧80% in water in 30 minutes at 37° C. which comprises the steps of (i) providing cefaclor material having a dissolution rate in a capsule of <80% in water in 30 minutes at 37° C.; and (ii) reducing the water content of the cefaclor material to produce a cefaclor form having a water content ≦2%. The material produced having a water content ≦2% may optionally be rehydrated to a water content from about 3.0% to about 6.5%. The cefaclor material having a dissolution rate in a capsule of <80% in water in 30 minutes at 37° C. may be characterized by: the presence of a near infrared reflectance (NIR) absorbance at 5798 cm$^{-1}$ (1725 nm) either initially or within 5 minutes after the addition of water to the sample (i.e., NIR onset time <5 minutes); having a non-homogenous water content (e.g., lots containing residual dihydrate starting materials); or agglomerates upon addition of water.

In another embodiment of the present invention, a process for producing cefaclor crystalline bulk form having a dissolution rate in a capsule of ≧80% in water in 30 minutes at 37° C. which comprises the steps of (i) providing cefaclor dihydrate; and (ii) reducing the water content of the cefaclor dihydrate to produce a cefaclor form having a water content ≦2%.

In yet another embodiment of the present invention, a process is provided for producing cefaclor crystalline bulk form having a dissolution rate in a capsule of ≧80% in water in 30 minutes at 37° C. which comprises the steps of (i) providing cefaclor bulk material having a dissolution rate in a capsule of <80% in water in 30 minutes at 37° C.; and (ii) adding ≧0.05% of cefaclor related substances.

Crystalline cefaclor bulk materials and capsules prepared therefrom having a dissolution rate in a capsule of ≧80% in water in 30 minutes at 37° C. prepared by the processes described above are also provided. One can also use the crystalline cefaclor bulk materials prepared by the processes described herein in other oral formulations such as tablets and liquid suspensions.

Definitions

As used herein, "cefaclor crystalline bulk form" or "cefaclor crystalline bulk material" refers to a mixture of a non-stoichiometric cefaclor monohydrate and anhydrous cefaclor.

"NIR onset time" refers to the time between addition of water to a cefaclor sample and the observation of an absorption peak at about 5798 cm$^{-1}$ (1725 nm) as measured by Near-Infrared Reflectance Spectroscopy (NIRS). Depending upon the particular instrument used, the exact peak measurement may vary within the standard deviation established for that particular instrument.

"Cefaclor related substances" refers to degradation products of cefaclor that are structurally related to the pharmaceutically active cefaclor compound. For example, related substances include compounds such as the $\Delta^2$-isomer of cefaclor, the decarboxylated derivative of cefaclor, and other similar degradation products.

Figure 1:
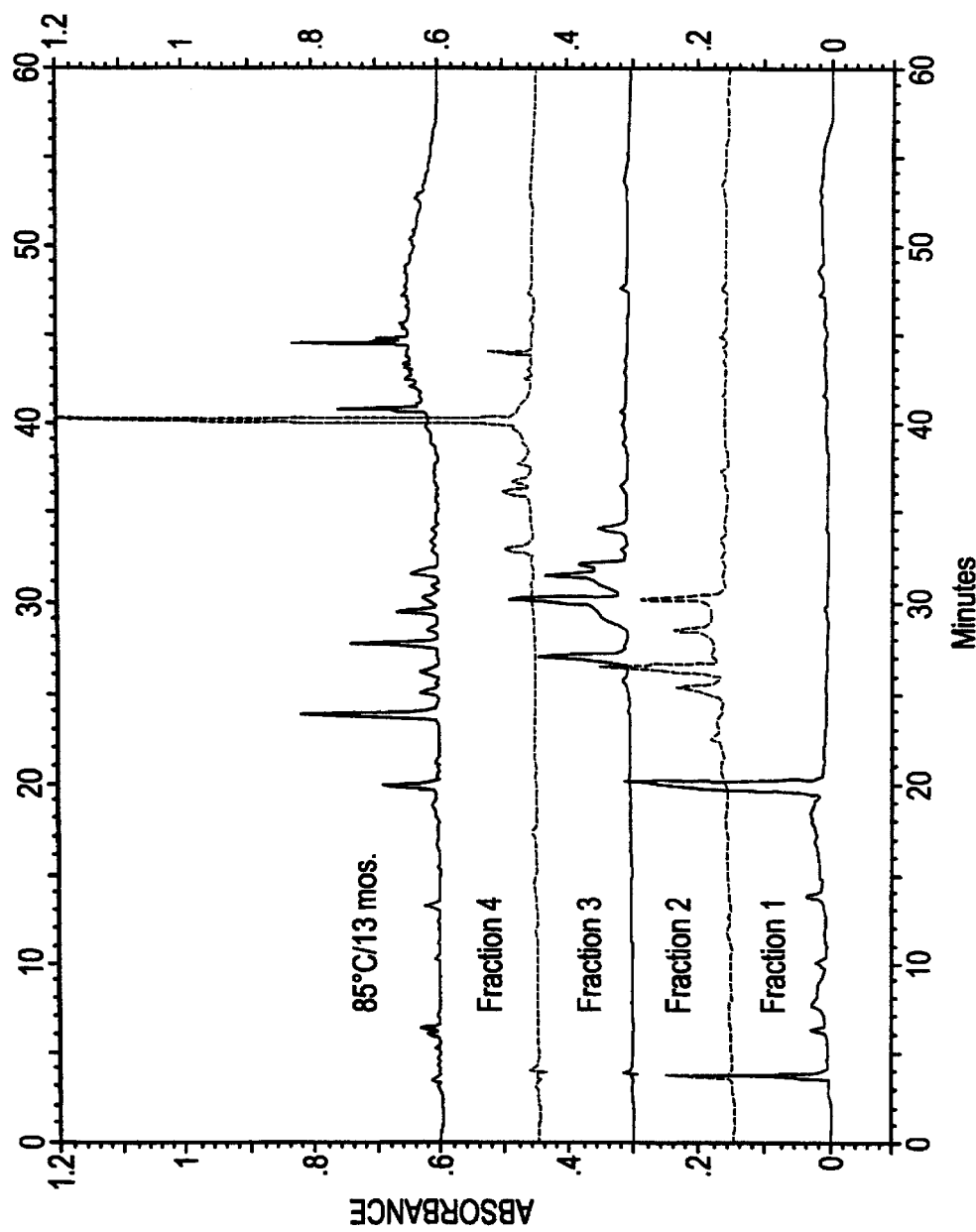
FIG. 1 illustrates the HPLC chromatograms (UV detection, 220 nm) of preparative HPLC fractions 1–4 overlaid with the chromatogram from the 85° C.-degraded sample.

Applicants discovered a change in dissolution rate of capsules manufactured with freshly prepared cefaclor crystalline bulk material versus capsules prepared from aged cefaclor crystalline bulk material. In the manufacture of cefaclor bulk, the product is crystallized from an aqueous system as a dihydrate crystal form. The cefaclor dihydrate is then converted to the cefaclor crystalline bulk form (mixture of a non-stoichiometric cefaclor monohydrate and anhydrous cefaclor) by partially removing water (e.g., fluid bed dryer) from the dihydrate crystalline material. Using X-ray diffraction (XRD) spectroscopy, Applicants discovered that samples of some lots of cefaclor bulk changed crystal form from the monohydrate back to the dihydrate within minutes after exposure to water (e.g., a NIR peak at 5798 cm$^{-1}$ is observed); whereas, the crystal form of other bulk lots did not convert back to the dihydrate form. Applicants have found that there is a strong correlation between the dissolution rate of the capsules and the different conversion rates (i.e., rate of conversion from the monohydrate form to the dihydrate form) of the lots from which the capsules are made.

Through X-ray diffraction studies of readily dissolving and incompletely dissolving lots of cefaclor, it was determined that all lots are initially in the same crystallographic state (monohydrate). Upon addition of water to readily dissolving lots, there is no change in the X-ray powder diffraction pattern over a five minute period. In contrast, when water is added to incompletely dissolving lot of cefaclor, substantial amounts of the dihydrate form are detected in less than five minutes. In an older lot of cefaclor, no dihydrate was detected for as long as two days, at which time the study was discontinued.

Although not wanting to be bound by any particular theory, Applicants believe that the change in dissolution rate is caused by the crystal form transformation of the cefaclor bulk back to the dihydrate form. The dihydrate form is less readily soluble in water than the monohydrate form. An accelerated conversion of the monohydrate to the dihydrate form upon exposure to water is believed to cause the formulated material to agglomerate into a hard plug of material in the dissolution testing apparatus, thus inhibiting it from dispersing and dissolving. The conversion rate of the monohydrate to the dihydrate form has been shown to be enhanced by increasing the concentration of amorphous cefaclor and/or dihydrate seeds, and inhibited by increasing the concentration of cefaclor related substances. Additional drying of the bulk to a water content less than or equal to 2% provided cefaclor bulk material having an improved dissolution rate in capsules. It is believed that the additional drying process removes traces of cefaclor dihydrate thus reducing the potential for seeding crystallization of the dihydrate form. Once the material is dried to a water content of $\leq 2\%$, the material can be surprisingly rehydrated to a water content from about 3.0 to about 6.5% (preferably from about 3.0% to 5.0%, more preferably from about 3.0% to 4.5%) without causing the material to fail the dissolution test. One can rehydrate to a higher water content (i.e., >6.5%); however, the USP standard for cefaclor monohydrate sets a range between 3.0% and 6.5%. It is preferable to rehydrate the material to achieve a more stable form since the bulk material is hygroscopic at lower water contents.

For investigational purposes, a dissolution model test was developed for capsules filled in the laboratory with the drug substance only. A second test was developed to qualitatively determine the tendency of a bulk lot to agglomerate when wetted (aqueous dispersability test). In order to assess the propensity of a given bulk lot toward reversion to the dihydrate crystal form when wetted, a test was ultimately developed using Near-Infrared Reflectance Spectroscopy (NIRS). NIRS readily distinguishes between the dihydrate, monohydrate, and anhydrate forms of cefaclor. Unlike the anhydrous and monohydrate forms, the dihydrate form has a relatively strong absorbance at about 5798 cm$^{-1}$ which provides an excellent indicator for the presence of the dihydrate form in the sample. Each of the tests described above are described in more detail in the Example section.

The NIRS conversion test measures the time in minutes before the onset of the crystal form reversion for a sample of cefaclor bulk. The NIR onset time was found to be an indicator of the dissolution assay result for a given bulk lot. Lots exhibiting longer NIR onset times (>about 5 minutes) were less likely to agglomerate during the dissolution test, whereas lots with short NIR onset times (<about 5 minutes) were more likely to revert to the dihydrate during the dissolution test, forming a plug of non-dispersing agglomerated material prior to complete dissolution of the capsule shell. To ensure that a lot will have an acceptable dissolution rate, one generally strives for a NIR onset time of >7 minutes, preferably >9 minutes and more preferably >10 minutes.

Using the indicator tests, the dihydrate reversion time was found to be delayed or the reversion altogether inhibited by addition of cefaclor related substances to a cefaclor bulk sample; whereas, the addition of amorphous cefaclor and/or cefaclor dihydrate was found to decrease the reversion onset time thus accelerating the crystal form conversion. The effects seen by the addition of the cefaclor related substances, amorphous cefaclor and/or cefaclor dihydrate can be explained by a classical crystallization model: 1) additional amorphous cefaclor increases the level of cefaclor supersaturation in a wetted sample; 2) the dihydrate serves as a source of seed for the recrystallization as dihydrate; and 3) the artificially induced (higher) levels of related substances inhibit growth of new dihydrate crystals. This model was applied to explain the improvement in dissolution assay with the age of the bulk lot, and conversely explain why the capsule dissolution assays trended downward as the bulk age decreased. The amount of amorphous material in a given lot would decrease by decomposition or by relaxation to a lower energy state. Any residual dihydrate seed would be expected to continue to convert to the bulk form, as supported by thermodynamic and kinetic studies showing the dihydrate spontaneously dehydrates below a critical relative humidity.

Through microcalorimetry, it has been shown that both acceptable and unacceptable lots of cefaclor monohydrate possess between 1.6% to 3.2% amorphous character. Therefore, the presence of amorphous material alone is probably not the cause of poor dissolution rates. However, the presence of amorphous character may contribute to poor dissolution rates especially when located on the surface of the crystalline material and/or in the presence of the dihydrate form.

Freshly manufactured lots were observed to convert to the dihydrate within about 2 minutes and nearly completed conversion in about 4 minutes. After 28 days of aging, samples were observed to convert at approximately 6 minutes and completed conversion at around 12 minutes. Although storage of the bulk material for 35 days increased the dissolution rate of the resultant capsules to an acceptable level, this was obviously not a desirable approach for the reasons discussed in the background.

A study of additional drying of cefaclor bulk in a laboratory rotary vacuum dryer (RVD) demonstrated that the performance of the bulk in the dissolution model tests improved with additional drying. Drying time and temperature were found to impact the NIR onset time. An increase in total related substances was also noted at elevated drying temperatures. A study of additional drying of cefaclor bulk in a laboratory vacuum drying oven demonstrated a relationship between the water content of the bulk at the end of drying and the NIR onset time. The lower the ending water content, the longer the NIR onset time.

Based on the promising results of the laboratory based studies, lots of cefaclor bulk were prepared at production scale wherein the cefaclor was dried to a water content of 2% or less, followed by rehydration to a water content range from 3.0% to 6.5%. These lots were then formulated into 500 mg capsules. The change in NIR onset time of lots which have been overdried and rehydrated were compared over time with lots dried only to a water content of 3.0% to 6.5%. The NIR onset time for lots overdried and then rehydrated were initially much longer than typically observed for lots dried only to between 3.0% and 6.5% water content, indicating the desired effect had been achieved, and that a prediction of improved dissolution could be made. When these lots were formulated and filled into 500 mg capsules, improved dissolution rates were indeed observed.

Although this experiment concentrated on 500 mg capsules, the same trends would be expected in other sized capsules (e.g., 150 mg, 250 mg, and 300 mg capsules).

It has also been hypothesized that the presence of cefaclor related substances may influence the dissolution performance. It has been observed that the $\Delta^2$-isomer, a known degradation product of cefaclor, influences the solubility versus time profiles of cefaclor in a manner which is consistent with inhibition of the recrystallization process (i.e., conversion of monohydrate to dihydrate). A study was conducted to determine if degradation products of cefaclor might have an inhibitory effect on the rate of conversion of cefaclor to the dihydrate form. In the first study, a crystalline sample of the $\Delta^2$-isomer (1) was used.

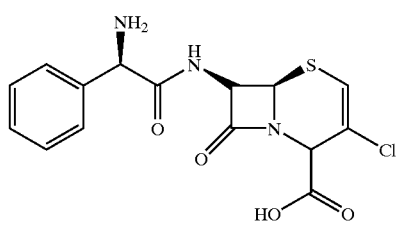

1

The $\Delta^2$-isomer was added to a poorly dissolving lot of cefaclor at 0.5% concentration by weight. The sample was mixed in the dry state. After addition of 1 ml of water to a 0.80 g sample, the X-ray diffraction pattern was collected at different time intervals. It was found that there was a minor inhibitory effect. The addition of the $\Delta^2$-isomer may have had a more significant effect if the material was mixed in a liquid rather than in a dry state.

Figure 2:
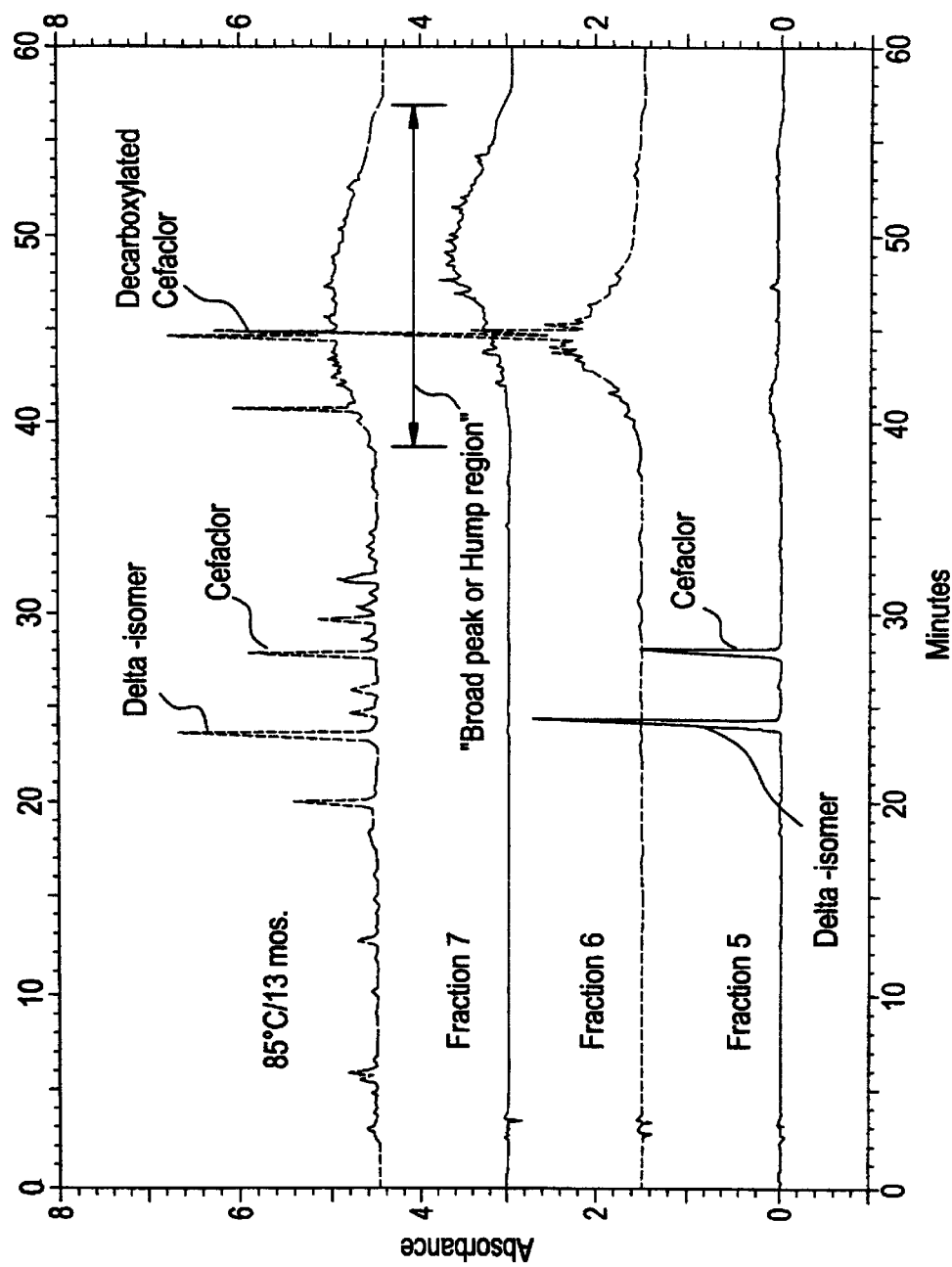
FIG. 2 illustrates the HPLC chromatograms (UV detection, 220 nm) of preparative HPLC fractions 5–7 overlaid with the chromatogram from the 85° C.-degraded sample.

When a badly degraded sample of cefaclor was added, a significant improvement in dissolution rate was observed. A sample of a highly degraded lot of cefaclor (degraded at 85° C. for 13 months) was fractionated by preparative HPLC to determine which degradation products are responsible for the inhibitory activity. (Preparative HPLC: 50×250 mm Kromasil C-18 column with a 10 mM particle size; gradient elution scheme 95-5/5-95 0.1% trifluoroacetic acid (TFA) in water/ 0.1% TFA in acetonitrile; and flow rate=49.9 ml/min.)) The degraded cefaclor sample was subdivided into seven different fractions (see, FIGS. 1 and 2) and tested for inhibitory activity. While each of the fractions showed some inhibitory activity, fractions 5 and 6 were the most potent. Fraction 5 consists of two main peaks, the $\Delta^2$-isomer of cefaclor (1) and cefaclor itself, along with a small amount of the front part of a "broad peak" region. Fraction 6 also contains a significant amount of the front part of the "broad peak" region along with decarboxylated cefaclor (2) and smaller amounts of other degradation products of cefaclor which are unidentified.

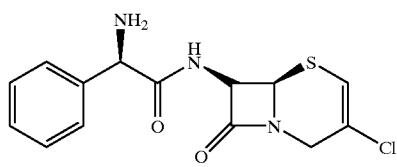

2

Kinetic studies were carried out using fraction 6 to gain a better understanding of how much would be required to achieve acceptable results in the model dissolution test. It was found that there was a measurable inhibitory effect down to a level of 0.05% by weight, based on the X-ray diffraction conversion rate test.

A dissolution study indicated that samples that are spiked with fraction 6 at levels of 0.2% and 0.1% provided sufficient conversion inhibition to achieve greater than 90% dissolution in fifteen minutes, thus passing the model dissolution test. The 0.05%-spiked sample passed the model dissolution criteria of 80% in thirty minutes, but not nearly to the extent that the 0.1 and 0.2% spiked samples did (81% as compared to 99 and 98%). The cefaclor sample without added related substances failed the dissolution test (78% dissolved in thirty minutes). Therefore, a lot of cefaclor bulk material that fails the dissolution test can be made acceptable by the addition of at least 0.05% of total related substances to the bulk material. Technically, there is no real upper limit. However, the quality and potency of the drug will be reduced at the higher percentages of added related substances. Consequently, the addition of related substances should preferably not exceed 5.0%, more preferably 3.0% and most preferably 2.0%.

Alternatively, one can generate additional related substances by heating the bulk material. Therefore, the term "adding related substances" includes not only the physical addition of related substances but also addition by means of heating the material to generate the related substances. The preferred means is by adding the related substances physically since one would have more control over the amounts added.

The pharmaceutical formulation has also been observed to exhibit faster capsule dissolution rates when the formulation mix is aged priori to filling into capsules. Although the mechanism of this aging phenomenon is not currently known, one can reasonably speculate that the effect of aging the formulation is the same as that observed in the aging of bulk cefaclor. Dihydrate seeds whether in the bulk or in the pharmaceutical mix would have a potential effect on the dissolution rates of cefaclor capsules. The lower the level of dihydrate seed, the less the effect on capsule dissolution rates. From a thermodynamic perspective, dihydrate seeds may be removed by slow equilibration (or aging). Thus an additional short aging step, either at the bulk or at the mixing step (or even at the capsule stage) would allow time for the residual dihydrate seeds to convert to cefaclor bulk via the thermodynamic process.

Alternatively, the observation might be related to the hygroscopicity of cefaclor bulk. For example, there might be some redistribution of water between cefaclor and the excipients. Thus, the dissolution characteristics of the excipient(s) might contribute to the observed effects.

As another alternative, the process of mixing may be causing some shearing and grinding of the cefaclor crystals thus increasing the amount of amorphous material. Grinding is well known to increase the disorder and/or amorphous character of crystalline materials. The hold time following mixing of the formulation would allow time for the high-energy materials and/or amorphous cefaclor to relax.

A process for preparing cefaclor capsules having a dissolution rate in a capsule of ≧80% in water in 30 minutes at 37° C. includes the steps of (i) providing a cefaclor bulk form prepared by any of the processes described herein; (ii) mixing the cefaclor bulk form with a pharmaceutically acceptable carrier to form a mixture; and (iii) filling a capsule with the mixture. Suitable pharmaceutically acceptable carriers (including diluents and excipients) are well known to those skilled in the art and include materials such as carbohydrates, waxes, water soluble and/or swellable polymers, hydrophilic or hydrophobic materials, gelatin, oils, and the like. The formulations may also include wetting agents, lubricating agents, emulsifiers, suspending agents, preservatives, sweeteners, perfuming agents, flavoring agents and combinations thereof.

EXAMPLES

Cefaclor dihydrate may be prepared from the anhydrate, monohydrate or solvate (e.g., the solvate described in Example 4 of U.S. Pat. No. 5,608,055) using the general procedures described in Martinex, Heriberto, et al., "Solid-state Chemistry and Crystal Structure of Cefaclor Dihydrate", Pharm. Res. 7(2), 147–53 (1990). Cefaclor anhydrate, monohydrate or solvate is dissolved in 1M HCl (pH approximately 1.4). Activated charcoal is added to the solution and filtered. The pH of the filtered solution is raised to about 3.6 to 4.5 by adding ammonium hydroxide. The cefaclor dihydrate is then crystallized from the solution by cooling the slurry to about 0° C. to 20° C.

Analytical Testing Methods

Model Dissolution Test

Approximately 523 mg of bulk cefaclor is filled into an empty 500 mg cefaclor capsule (KG3062). The USP monograph dissolution test is then performed with filtered samples being withdrawn at 15, 30, and 45 minutes. The test conditions are USP Apparatus 2 at 50 rpm using 900 ml of purified water maintained at 37° C. Visual examination is done at the time of sample collection. Visual observations range from "the material is completely dissolved and/or dispersed within 5 minutes with no visible residue or agglomerates to a large intact mass remains at the end of 45 minutes that is hard to the touch." An ultraviolet (UV) assay is conducted on the filtered aliquots to determine the percent dissolution.

Aqueous Dispersibility Test

Approximately 100 mg of bulk cefaclor is placed on a glass slide. De-ionized water (approximately 6 drops) is added to the edge of the cefaclor. After five minutes of exposure to water, a glass slide cover slip is used to inspect the sample. A sample fails if the sample agglomerates. A sample passes if the wet-bulk cefaclor is flowable in nature.

Near Infrared Dihydrate Conversion Test

Approximately 1 to 2 grams of sample was spread in a thin layer on the bottom of an open aluminum weighing pan and placed in a constant humidity chamber, containing a saturated aqueous solution of $K_2HPO_4$, for at least two hours prior to analysis. Following equilibration in the humidity chamber, the sample was packed into a 2 mm×6 mm, stainless steel sample cup until full (approximately 35 mg), and 6 $\mu$L of water placed in the center of the sample. NIR data were collected using the NIR Systems model 5000 equipped with a fiber optic diffuse-reflectance probe, positioned over the sample cup. Immediately following addition of the water, NIR spectra were recorded from 1100 to 2500 nm approximately each 30 seconds. The time elapsed prior to the first appearance of the dihydrate peak at 1725 nm (5798 cm$^{-1}$) was reported as the NIR onset time.

USP 23 Standard Dissolution Test for Cefaclor Capsules

Dissolution (711): The test conditions are USP Apparatus 2 at 50 rpm using 900 ml of purified water maintained at 37° C. for 30 minutes. Determine the amount of Cefaclor monohydrate dissolved from ultraviolet absorbances at the wavelength of maximum absorbances at about 264 nm of filtered portions of the solution under test, suitably diluted with water, in comparison with a Standard solution having a know concentration of USP Cefaclor RS in the same medium.

Dissolution testing is continued with additional units through three stages unless the results conform at either the 1$^{st}$ or 2$^{nd}$ stage according to the following acceptance

TABLE 1

| Stage | Number Tested | Acceptance Criteria |
|---|---|---|
| S1 | 6 | Each unit is not less than Q + 5% |
| S2 | 6 | Average of 12 units (S1 + S2) is equal to or greater than Q, and no unit is less than Q − 15% |
| S3 | 12 | Average of 24 units (S1 + S2 + S3) is equal to or greater than Q, not more than 2 units are less than Q − 15%, and no unit is less than Q − 25% |

The quantity, Q, is the % of dissolved active ingredient in the specification. For Cefaclor, at Stage 1, each individual unit must be at least 85% dissolved in 30 minutes to pass the testing. If any of the 6 units tested is less than 85% dissolved, the product fails level S1 and you must go to S2. At Stage 2, the mean of the twelve units tested (first 6 from S1 and 6 from S2) must be at least 80% dissolved and no unit may be less than 65% dissolved. If these criteria are not met, the product fails the level S2 specification and you must go to S3. At Stage 3, the mean of the 24 units tested (6 from S1+6 from S2+12 from S3) must be at least 80% dissolved, no more than 2 units may be less than 65% dissolved, and none of the units may be less than 55% dissolved.

Examples 1 and 2 compare the results of monohydrate bulk materials generated by the old method (control) with the dehydration process and the dehydration/rehydration process for improving the dissolution rate.

Preparation of Cefaclor Monohydrate (Control)

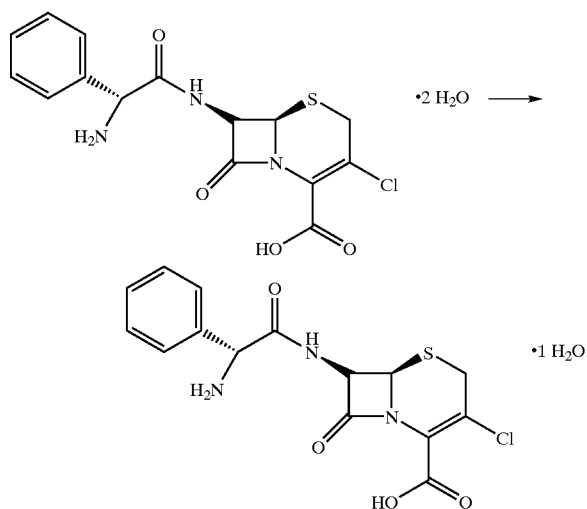

Cefaclor dihydrate is dried in a fluidized bed at not more than 70° C. (refers to product temperature) to a water content range of 3.0 to 6.5% water by Karl Fischer analysis. Bulk material produced using this method had an average NIR onset time of 1.2 minutes with an upper control limit of approximately 2.5 minutes.

Example 1

Example 1 illustrates the effect on NIR onset time when a sample of cefaclor dihydrate is dried to a lower water content using the same procedures as described in the control above with longer drying times. Table 2 summarizes the NIR onset times observed at the corresponding water contents of the resultant cefaclor monohydrate.

TABLE 2

| Sample Number | Karl Fischer Analysis (K. F.) | NIR Onset Time |
|---|---|---|
| 1-1 | 2.7% | 3 minutes |
| 1-2 | 1.7% | 11 minutes |
| 1-3 | 3.3% | 2.5 minutes |

The results in Table 2 clearly show that drying a sample of cefaclor dihydrate to a water content less than 2% has a significant effect on the NIR onset time.

Example 2

Example 2 illustrates the process for producing cefaclor bulk material that has been dehydrated and then rehydrated back to a water content between 3.0 and 6.5%.

Cefaclor dihydrate is dried in a fluidized bed at not more than 70° C. (refers to product temperature) to a lower water content under two different drying conditions: Condition #1—NMT 10 grains of moisture/pound of dry air (full desiccation); and Condition #2—NMT 40 grains of moisture/pound of dry air. The resultant product is then rehumidified with humidified air to a water content between 3.0 to 6.5%. Tables 3 and 4 summarize the dissolution rates of capsules made from bulk materials produced by the dehydration/rehydration process described above.

TABLE 3

Analysis of Capsule Dissolution Rates From Bulk Cefaclor Lots Dried Utilizing Full Desiccation Dried Air Followed by Rehydration

| Sample # | Water Content after Drying (lowest K. F. #) | Water Content after Rehydration (K. F. #) | 1st stage | 2nd stage |
|---|---|---|---|---|
| 2-1a | 1.7% | 4.2% | 102 | N/A |
|  |  |  | 101 |  |
|  |  |  | 102 |  |
|  |  |  | 100 |  |
|  |  |  | 94 |  |
|  |  |  | 101 |  |
|  |  |  | 100 |  |
|  |  |  | (Avg. n = 6) |  |
| 2-1b | 1.9% | 3.6% | 91 | N/A |
|  |  |  | 85 |  |
|  |  |  | 88 |  |
|  |  |  | 96 |  |
|  |  |  | 95 |  |
|  |  |  | 92 |  |
|  |  |  | 90 |  |
|  |  |  | (Avg. n = 6) |  |
| 2-1c | 1.8% | 4.1% | 90 | N/A |
|  |  |  | 95 |  |
|  |  |  | 97 |  |
|  |  |  | 89 |  |
|  |  |  | 96 |  |
|  |  |  | 96 |  |
|  |  |  | 94 |  |
|  |  |  | (Avg. n = 6) |  |

TABLE 4

Analysis of Capsule Dissolution Rates From Bulk Cefaclor Lots Dried Utilizing 40 grains Dried Air Followed by Rehydration

| Sample # | Water Content after Drying (lowest K. F. %) | Water Content after Rehydration (K. F. %) | 1st stage | 2nd stage |
|---|---|---|---|---|
| 2-2a | 2.6% | 4.2% | 98 | 97 |
|  |  |  | 101 | 96 |
|  |  |  | 97 | 98 |
|  |  |  | 92 | 95 |
|  |  |  | 95 | 99 |
|  |  |  | 81 | 100 |
|  |  |  | 94 | 98 |
|  |  |  | (Avg. n = 6) | (Avg. n = 6) |
|  |  |  | 96 |  |
|  |  |  | (Avg. n = 12) |  |
| 2-2b | 2.7% | 3.6% | 80 | 104 |
|  |  |  | 97 | 95 |
|  |  |  | 84 | 94 |
|  |  |  | 90 | 69 |
|  |  |  | 101 | 87 |
|  |  |  | 94 | 86 |
|  |  |  | 91 | 89 |
|  |  |  | (Avg. n = 6) | (Avg. n = 6) |
|  |  |  | 90 |  |
|  |  |  | (Avg. n = 12) |  |
| 2-2c | 2.4% | 3.6% | 94 | 103 |
|  |  |  | 75 | 98 |
|  |  |  | 86 | 88 |
|  |  |  | 91 | 96 |
|  |  |  | 92 | 87 |
|  |  |  | 96 | 96 |
|  |  |  | 89 | 95 |
|  |  |  | (Avg. n = 6) | (Avg. n = 6) |
|  |  |  | 92 |  |
|  |  |  | (Avg. n = 12) |  |

Tables 3 and 4 show that rehydration of the bulk material that was produced under either condition 1 or 2 had little effect on the dissolution rate of the capsules. No failures were observed when the bulk material was dried to <2.0% under full desiccation conditions and then rehydrated. Some failures were noted when the bulk material was dried under condition 2 (40 grains of moisture/pound of dry air). It is very difficult to reach water contents less than 2% under this drying condition. The lowest water content observed for samples 2–2a through 2–2c was 2.6%, 2.7% and 2.4% respectively. Although acceptable material may be produced at water contents less than 3.0%, preferably the water content is reduced to less than 2.0%.

We claim:

1. A process for producing cefaclor crystalline bulk form having a dissolution rate in a capsule of ≧80% in water in 30 minutes at 37° C. comprising the steps of
  (i) providing cefaclor material having a dissolution rate in a capsule of <80% in water in 30 minutes at 37° C.; and
  (ii) reducing the water content of said cefaclor material to produce a cefaclor form having a water content ≦2%.

2. The process of claim 1 further comprising step (iii) rehydrating said cefaclor form having a water content ≦2% to a water content from 3.0 to 6.5%.

3. A process for producing cefaclor crystalline bulk form having a dissolution rate in a capsule of ≧80% in water in 30 minutes at 37° C. comprising the steps of
  (i) providing cefaclor material having a near infrared reflectance absorbance at 5798 cm$^{-1}$ either initially or <5 minutes after the addition of water to said cefaclor material; and
  (ii) reducing the water content of said cefaclor material to produce a cefaclor form having a water content ≦2%.

4. The process of claim 3 further comprising step (iii) rehydrating said cefaclor form having a water content ≦2% to a water content from 3.0 to 6.5%.

5. A process for producing cefaclor crystalline bulk form having a dissolution rate in a capsule of ≧80% in water in 30 minutes at 37° C. comprising the steps of
   (i) providing cefaclor dihydrate; and
   (ii) reducing the water content of said cefaclor dihydrate to produce a cefaclor form having a water content ≦2%.

6. The process of claim 5 further comprising step (iii) rehydrating said cefaclor form having a water content ≦2% to a water content from 3.0 to 6.5%.

7. A process for producing cefaclor crystalline bulk form having a dissolution rate in a capsule of ≧80% in water in 30 minutes at 37° C. comprising the steps of:
   (i) providing cefaclor monohydrate bulk material having a dissolution rate in a capsule of <80% in water in 30 minutes at 37° C.; and
   (ii) adding at least 0.05% of cefaclor related substances.

8. The process of claim 7 wherein 0.05% to 5.0% of cefaclor related substances is added in step (ii).

9. The process of claim 7 wherein 0.05% to 3.0% of cefaclor related substances is added in step (ii).

10. The process of claim 7 wherein 0.05% to 2.0% of cefaclor related substances is added in step (ii).

11. A crystalline bulk form of cefaclor having a NIR onset time of ≧5 minutes prepared by the steps of:
    (i) providing cefaclor material having a dissolution rate in a capsule of <80% in water in 30 minutes at 37° C.; and
    (ii) reducing the water content of said cefaclor material to produce a cefaclor form having a water content ≦2%.

12. The crystalline bulk form of claim 11 further comprising step (iii) rehydrating said cefaclor form having a water content ≦2% to a water content from 3.0 to 6.5%.

13. A crystalline bulk form of cefaclor having a NIR onset time of ≧5 minutes prepared by the steps of:
    (i) providing cefaclor material having a near infrared reflectance absorbance at 5798 cm$^{-1}$ either initially or less than 5 minutes after the addition of water to said cefaclor material; and
    (ii) reducing the water content of said cefaclor material to produce a cefaclor form having a water content ≦2%.

14. The crystalline bulk form of claim 13 further comprising step (iii) rehydrating said cefaclor form having a water content ≦2% to a water content from 3.0 to 6.5%.

15. A crystalline bulk form of cefaclor having a NIR onset time of ≧5 minutes prepared by the steps of:
    (i) providing cefaclor dihydrate; and
    (ii) reducing the water content of said cefaclor dihydrate to produce a cefaclor form having a water content ≦2%; and
    (iii) rehydrating said cefaclor form having a water content ≦2% to a water content from 3.0 to 6.5%.

16. The crystalline bulk form of claim 15 further comprising step (iii) rehydrating said cefaclor form having a water content ≦2% to a water content from 3.0 to 6.5%.

17. A process for preparing cefaclor capsules having a dissolution rate in a capsule of ≧80% in water in 30 minutes at 37° C. comprising the steps of
    (i) providing a cefaclor crystalline bulk form prepared by any of the processes of claims 1, 3, 5 or 7;
    (ii) mixing said cefaclor crystalline bulk form with a pharmaceutically acceptable carrier to form a mixture; and
    (iii) filling a capsule with said mixture.

* * * * *